United States Patent
Dong

(10) Patent No.: US 11,653,873 B2
(45) Date of Patent: May 23, 2023

(54) SKIN DETECTION DEVICE AND PRODUCT INFORMATION DETERMINATION METHOD, DEVICE AND SYSTEM

(71) Applicant: BOE TECHNOLOGY GROUP CO., LTD., Beijing (CN)

(72) Inventor: Wenchu Dong, Beijing (CN)

(73) Assignee: BOE TECHNOLOGY GROUP CO., LTD., Beijing (CN)

( * ) Notice: Subject to any disclaimer, the term of this patent is extended or adjusted under 35 U.S.C. 154(b) by 1197 days.

(21) Appl. No.: 16/309,269

(22) PCT Filed: Jan. 11, 2018

(86) PCT No.: PCT/CN2018/072176
§ 371 (c)(1),
(2) Date: Dec. 12, 2018

(87) PCT Pub. No.: WO2019/000908
PCT Pub. Date: Jan. 3, 2019

(65) Prior Publication Data
US 2019/0374156 A1    Dec. 12, 2019

(30) Foreign Application Priority Data
Jun. 29, 2017    (CN) .......................... 201710517873.3

(51) Int. Cl.
*A61B 5/00*    (2006.01)
*G06T 7/90*    (2017.01)
(Continued)

(52) U.S. Cl.
CPC ............ *A61B 5/442* (2013.01); *A61B 5/0053* (2013.01); *A61B 5/0077* (2013.01); *A61B 5/053* (2013.01);
(Continued)

(58) Field of Classification Search
None
See application file for complete search history.

(56) References Cited

U.S. PATENT DOCUMENTS 5,938,593 A * 8/1999 Ouellette ............. A61B 5/7435
324/692
6,571,003 B1 * 5/2003 Hillebrand ............. A61B 5/442
382/118
(Continued)

FOREIGN PATENT DOCUMENTS

CN    1355680 A    6/2002
CN    2708308 Y    7/2005
(Continued)

OTHER PUBLICATIONS

International Search Report and Written Opinon dated Apr. 19, 2018.
(Continued)

*Primary Examiner* — Ricky Chin
(74) *Attorney, Agent, or Firm* — Dilworth & Barrese, LLP.; Michael J. Musella, Esq.

(57) ABSTRACT

A skin detection device, including a processor and a texture recognition sensor, is disclosed. The texture recognition sensor is configured to detect surface texture of skin to be detected; and the processor is configured to determine surface smoothness of the skin to be detected according to the surface texture of the skin to be detected. The skin detection device can independently perform the health detection of the skin to be detected. A product information determination method, a product information determination device and a product information determination system are further disclosed.

16 Claims, 10 Drawing Sheets

(51) Int. Cl.
*A61B 5/053* (2021.01)
*A61B 5/16* (2006.01)
*G06Q 30/0601* (2023.01)
*G09B 19/00* (2006.01)
*G06V 40/16* (2022.01)

(52) U.S. Cl.
CPC .............. *A61B 5/165* (2013.01); *A61B 5/443* (2013.01); *A61B 5/444* (2013.01); *A61B 5/7275* (2013.01); *G06Q 30/0623* (2013.01); *G06T 7/90* (2017.01); *G06V 40/174* (2022.01); *G09B 19/00* (2013.01); *G06T 2207/10024* (2013.01); *G06T 2207/30088* (2013.01); *G06V 40/178* (2022.01)

(56) References Cited

U.S. PATENT DOCUMENTS

| | | | | |
|---|---|---|---|---|
| 6,904,408 | B1* | 6/2005 | McCarthy | A61B 5/6815 705/2 |
| 7,087,019 | B2* | 8/2006 | Kao | A61B 5/442 324/692 |
| 2002/0107456 | A1* | 8/2002 | Leveque | A61B 5/441 600/587 |
| 2004/0125996 | A1* | 7/2004 | Eddowes | A61B 5/6888 382/128 |
| 2005/0159655 | A1* | 7/2005 | Kao | A61B 5/442 600/306 |
| 2006/0239547 | A1* | 10/2006 | Robinson | G06T 7/90 382/162 |
| 2008/0194928 | A1* | 8/2008 | Bandic | A61B 5/443 600/306 |
| 2010/0185064 | A1* | 7/2010 | Bandic | A61B 5/444 600/306 |
| 2011/0016001 | A1* | 1/2011 | Schieffelin | A61B 5/442 705/14.66 |
| 2011/0300196 | A1* | 12/2011 | Mohammadi | A61K 8/0212 118/712 |
| 2012/0041282 | A1* | 2/2012 | Nichol | A61B 5/448 600/306 |
| 2012/0179231 | A1* | 7/2012 | Dewaegenaere | A61F 7/10 607/104 |
| 2013/0245388 | A1* | 9/2013 | Rafferty | A61B 5/6831 600/307 |
| 2015/0045631 | A1* | 2/2015 | Ademola | A61B 5/443 600/301 |
| 2015/0173996 | A1* | 6/2015 | Grez | A61M 5/425 600/587 |
| 2015/0230863 | A1* | 8/2015 | Youngquist | A61B 18/203 606/9 |
| 2015/0356661 | A1* | 12/2015 | Rousay | G06V 40/168 705/26.7 |
| 2017/0031449 | A1* | 2/2017 | Karsten | G06Q 10/1095 |
| 2017/0035348 | A1* | 2/2017 | Bandic | A61B 5/443 |
| 2017/0076474 | A1* | 3/2017 | Fu | G06T 11/00 |
| 2017/0127998 | A1 | 5/2017 | Jang et al. | |
| 2017/0347939 | A1* | 12/2017 | Tang | A61B 5/1032 |
| 2018/0103891 | A1* | 4/2018 | Moon | A61B 5/0531 |
| 2019/0125249 | A1* | 5/2019 | Rattner | A61B 5/445 |
| 2019/0178764 | A1* | 6/2019 | Pelssers | A61B 5/442 |
| 2019/0298251 | A1* | 10/2019 | Kanaumi | A61B 5/0071 |
| 2019/0328997 | A1* | 10/2019 | Sunnen | A61M 21/02 |
| 2019/0343428 | A1* | 11/2019 | De Vries | A61B 5/6891 |
| 2019/0374156 | A1* | 12/2019 | Dong | A61B 5/0053 |
| 2020/0037882 | A1* | 2/2020 | Westerhof | A61B 5/0077 |
| 2020/0121941 | A1* | 4/2020 | Kwon | A61N 5/0616 |
| 2021/0150174 | A1* | 5/2021 | Fu | G06V 40/1318 |

FOREIGN PATENT DOCUMENTS

| | | |
|---|---|---|
| CN | 1723837 A | 1/2006 |
| CN | 101686819 A | 3/2010 |
| CN | 103717109 A | 4/2014 |
| CN | 103971270 A | 8/2014 |
| CN | 104840184 A | 8/2015 |
| CN | 105354527 A | 2/2016 |
| CN | 105979008 A | 9/2016 |
| CN | 205568944 U | 9/2016 |
| CN | 205697703 U | 11/2016 |
| CN | 106308793 A | 1/2017 |
| CN | 106659482 A | 5/2017 |
| CN | 106667431 A | 5/2017 |
| CN | 1020170057479 A | 5/2017 |
| DE | 102013201917 A1 | 8/2014 |
| KR | 101692444 B1 | 1/2017 |
| KR | 1020170022112 A | 3/2017 |
| WO | 02056766 A1 | 7/2002 |
| WO | 2015152028 A1 | 8/2015 |

OTHER PUBLICATIONS

Second Chinese Office Action from Chinese Patent Application 201710517873.3 dated Oct. 30, 2020.
European Search Report in European Patent Application No. 1884478.6 dated Feb. 25, 2021.
First Office Action in the priority Chinese application No. 201710517873.3 dated Mar. 2, 2020 and its English translation.
First Search Report in priority Chinese application No. 201710517873.3.

* cited by examiner

100

Acquiring collected data, in which the collected data includes: data, which is relevant to the skin to be detected and acquired by a skin detection device 401

Determining product information corresponding to at least one data in the collected data according to preset corresponding relationships between the data and the product information 402

SKIN DETECTION DEVICE AND PRODUCT INFORMATION DETERMINATION METHOD, DEVICE AND SYSTEM

TECHNICAL FIELD

Embodiments of the present disclosure relate to a skin detection device, a product information determination method, a product information determination device and a product information determination system.

BACKGROUND

With the improvement of people's living standard, people begin to pay more and more attention to their own health, and skin health is one of the key points. Detection of the health condition of the skin can be performed in a beauty agency, such that the health condition of the skin can be determined and the skin can be taken good care of by using a skin care product that corresponds to the health condition of the skin.

SUMMARY

Some embodiments of the present disclosure provide a skin detection device, a product information determination method, a product information determination device and a product information determination system. The technical solutions are described in the following.

At least one embodiment of present disclosure provides a skin detection device, and the skin detection device includes a processor and a texture recognition sensor. The processor is electrically connected with the texture recognition sensor; the texture recognition sensor is configured to detect surface texture of skin to be detected; and the processor is configured to determine surface smoothness of the skin to be detected according to the surface texture of the skin to be detected.

For example, the skin detection device further includes a first pressure sensor. The first pressure sensor is electrically connected with the processor and is configured to acquire pressure applied by the skin to be detected to the first pressure sensor when the skin detection device slides on the skin to be detected; and the processor is further configured to determine a value of elasticity of the skin to be detected according to the pressure acquired by the first pressure sensor.

For example, the skin detection device further includes a detection electrode electrically connected with the processor. The detection electrode is configured to acquire conductivity of the skin to be detected by contacting the skin to be detected; and the processor is further configured to determine moisture content and oil content of the skin to be detected according to the conductivity.

For example, the skin detection device further includes a base. The base includes a contact surface and a side surface, and the contact surface and the side surface are connected; the contact surface is configured to contact the skin to be detected; the texture recognition sensor and the detection electrode are disposed on the contact surface; and the first pressure sensor is disposed on the side surface.

For example, the skin detection device further includes a second pressure sensor. The second pressure sensor is disposed on the contact surface and configured to detect pressure applied to the second pressure sensor by a portion of the skin to be detected in contact with the contact surface; the processor is further configured to determine a target detection value according to the pressure detected by the first pressure sensor and the pressure detected by the second pressure sensor; and the processor is further configured to determine the value of elasticity of the skin to be detected according to the target detection value.

For example, a number of the second pressure sensors and a number of the first pressure sensors are identical; and the second pressure sensors are in one-to-one correspondence with the first pressure sensors.

For example, the texture recognition sensor is disposed in a central area of the contact surface; and the detection electrode is disposed in a periphery area of the contact surface.

For example, a material of the base is a flexible material; and the side surface is curved towards a side away from the skin to be detected, when the contact surface contacts the skin to be detected.

For example, the skin detection device further includes an image acquisitor electrically connected with the processor. The image acquisitor is configured to acquire an image of the skin to be detected; and the processor is further configured to determine colored patch distribution condition of the skin to be detected according to the image of the skin to be detected.

At least one embodiment of present disclosure provides a product information determination method, the product information determination method includes: acquiring collected data, in this step the collected data include data relevant to the skin to be detected and acquired by the skin detection device provided by the above-mentioned embodiments; and determining product information, corresponding to at least one of the data in the collected data, according to preset corresponding relationships between the data and the product information.

For example, after determining of the product information corresponding to the at least one of the data in the collected data, the method further includes: obtaining information of a target product set from information of at least one preset product set, in this step the information of the target product set includes the product information corresponding to the at least one of the data.

For example, after determining of the product information corresponding to the at least one of the data in the collected data, the method further includes: obtaining information of a target product set by redundancy elimination of the product information corresponding to the at least one of the data.

For example, after acquiring of the collected data, the method further includes: determining nursing advices corresponding to the at least one of the data according to preset corresponding relationships between the data and the nursing advices; and obtaining a target nursing advice through combining one or more of the nursing advices corresponding to the at least one of the data.

For example, the skin to be detected is skin of a target user; the collected data further include attribute data of the target user; and the attribute data include at least one of name, age, gender, preference and purchasing power.

For example, before acquiring of the collected data, the method further includes: acquiring verification information of the target user through a verification information acquisition device; and acquiring of the collected data includes: determining whether or not a plurality of preset historical verification information includes the verification information of the target user, and acquiring historical data corresponding to the verification information of the target user according to preset corresponding relationships between the historical verification information and the historical data in a case that the plurality of historical verification information includes the verification information of the target user. The collected data further include the historical data corresponding to the verification information of the target user.

For example, the method further includes: acquiring a face image of the target user through a camera; determining emotional level of the target user according to the face image of the target user; determining age bracket of the target user; determining target prompt words corresponding to the age bracket and the emotional level of the target user according to preset corresponding relationships between the prompt words and the age bracket, and between the prompt words and emotional level; and displaying at least one of the target prompt words, the target nursing advice, and the information of the target product set through an output device.

For example, the method further includes: acquiring an image of the skin to be detected through the skin detection device. After determining of the product information corresponding to the at least one of the data in the collected data, the method further includes: beautifying the image of the skin to be detected according to efficacy of the product information corresponding to the at least one of the data, and displaying a beautified image of the skin to be detected through the output device.

For example, acquiring of the collected data further includes: acquiring a target signal obtained by amplifying an initial signal through a signal amplifying device, in this step the initial signal includes the data relevant to the skin to be detected and acquired by the skin detection device; and extracting the data relevant to the skin to be detected from the target signal.

At least one embodiment of present disclosure provides a product information determination device, the product information determination device includes: a first acquisition module configured to acquire collected data, and the collected data include: data relevant to the skin to be detected and acquired by the skin detection device provided by the above-mentioned embodiments; and a first determination module configured to determine product information corresponding to at least one of the data in the collected data according to preset corresponding relationships between the data and the product information.

For example, the product information determination device further includes a screening module configured to obtain information of a target product set from information of at least one preset product set, and the information of the target product set includes the product information corresponding to the at least one of the data.

For example, the product information determination device further includes a redundancy elimination module configured to obtain information of a target product set by redundancy elimination of the product information corresponding to the at least one of the data.

For example, the product information determination device further includes a second determination module configured to determine nursing advices corresponding to the at least one of the data according to preset corresponding relationships between the data and the nursing advices; and a combination module configured to obtain a target nursing advice through combining one or more of the nursing advices corresponding to the at least one of the data.

For example, the skin to be detected is skin of a target user; the collected data further include attribute data of the target user; and attribute data include: name, age, gender, preference and purchasing power.

For example, the product information determination device further includes a second acquisition module configured to acquire verification information of the target user through a verification information acquisition device; the first acquisition module is further configured to: determine whether or not a plurality of preset historical verification information includes the verification information of the target user, and acquire historical data corresponding to the verification information of the target user according to preset corresponding relationships between the historical verification information and the historical data in a case that the plurality of historical verification information includes the verification information of the target user, and the collected data further include the historical data corresponding to the verification information of the target user.

For example, the product information determination device further includes an acquisition module configured to acquire a face image of the target user through a camera; a third determination module configured to determine emotional level of the target user according to the face image of the target user; a fourth determination module configured to determine age bracket of the target user; a fifth determination module configured to determine target prompt words corresponding to the age bracket and the emotional level of the target user according to preset corresponding relationships between the prompt words and the age bracket, and between the prompt words and emotional level; and a first display module configured to display at least one of the target prompt words, the target nursing advice, and the information of the target product set through an output device.

For example, the product information determination device further includes a third acquisition module configured to acquire an image of the skin to be detected through the skin detection device; a beautifying module configured to beautify the image of the skin to be detected according to efficacy of the product information corresponding to the at least one of the data; and a second display module configured to display a beautified image of the skin to be detected through the output device.

For example, the first acquisition module is further configured to: acquire a target signal obtained by amplifying an initial signal through a signal amplifying device, and extracting the data relevant to the skin to be detected from the target signal; and the initial signal includes the data relevant to the skin to be detected and acquired by the skin detection device.

At least one embodiment of present disclosure provides a product information determination system, and the product information determination system includes a skin detection device and a product information determination device provided by the above-mentioned embodiments. The skin detection device includes a processor and a texture recognition sensor; the texture recognition sensor is electrically connected with the processor and configured to detect surface texture of skin to be detected; and the processor is configured to determine surface smoothness of the skin to be detected according to the surface texture of the skin to be detected.

For example, the product information determination system further includes: a camera, an input device, an output device, a verification information acquisition device and a signal amplifying device. The camera is configured to acquire a face image of a target user, and the skin to be detected is skin of the target user; the input device is configured to input at least one of following information into the product information determination device: preset corresponding relationships between data and product information, preset corresponding relationships between the data and nursing advices, preset corresponding relationships between prompt words and age bracket, between prompt words and emotional level, information of at least one preset product set, and attribute data of the target user; the verification information acquisition device is configured to acquire verification information of the target user; the signal amplifying device is configured to amplify an initial signal and obtain a target signal and the initial signal includes data relevant to the skin to be detected and acquired by the skin detection device; and the output device is configured to display at least one of following information obtained by the product information determination device: target prompt words, a target nursing advice, information of a target product set, or a beautified image of the skin to be detected.

BRIEF DESCRIPTION OF THE DRAWINGS

In order to clearly illustrate the technical solution of the embodiments of the disclosure, the drawings used for describing the embodiments will be briefly described in the following; it is obvious to those skilled in the art that the described drawings are only related to some embodiments of the disclosure and other drawing(s) can be obtained based on the described drawings without any inventive work.

DETAILED DESCRIPTION

In order to make objects, technical details and advantages of the embodiments of the disclosure apparent, the technical solutions of the embodiments of the present disclosure will be described in detail with reference to the accompanying drawings.

The skin detection device in prior art cannot independently perform the detection of the skin health condition.

In a detection method, when a beautician of a beauty agency detects the condition of the skin to be detected, a skin detection device need to be used to acquire an enlarged image of the skin to be detected, and the enlarged image can reflect the subtle condition of the skin to be detected. Subsequently, the beautician can determine the health condition of the skin to be detected according to experience and the enlarged image.

In another detection method, the enlarged image (acquired by the skin detection device) of the skin cannot intuitively reflect the health condition of the skin, and the health condition of the skin to be detected can only be determined after the beautician analyzes the enlarged image. Both the above-mentioned two methods cannot independently perform the detection of the skin health condition.

Figure 1:
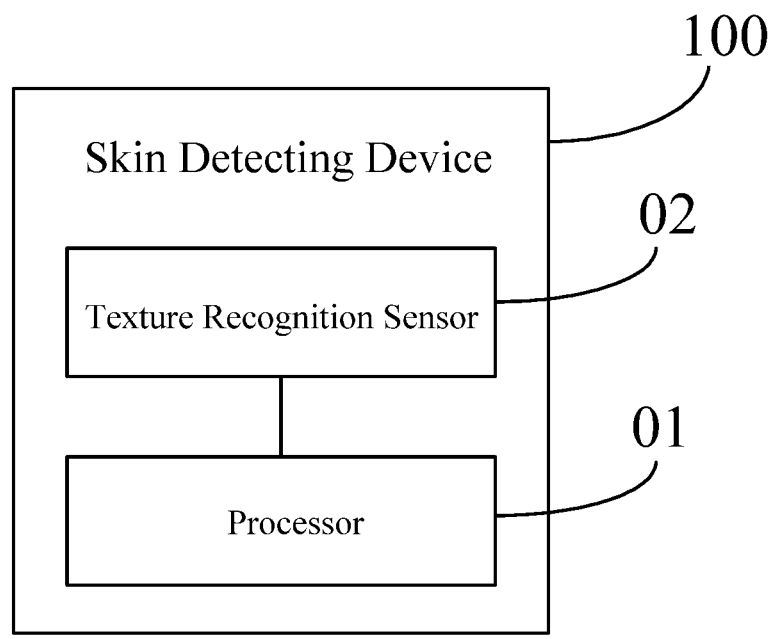
FIG. 1 is a schematic structural view of a skin detection device provided by the embodiments of the present disclosure.

FIG. 1 is a schematic structural view of a skin detection device provided by the embodiments of the present disclosure. As illustrated in FIG. 1, the skin detection device 100 can include a processor 01 and a texture recognition sensor 02. The processor 01 is electrically connected with the texture recognition sensor 02.

The texture recognition sensor 02 can be configured to detect the surface texture of the skin to be detected. The processor 01 can be configured to determine the surface smoothness of the skin to be detected according to the surface texture of the skin to be detected.

The skin detection device provided by the embodiments of the present disclosure includes a processor and a texture recognition sensor. The processor can determine the surface smoothness of the skin to be detected according to the surface texture of the skin to be detected, and the surface texture of the skin to be detected is detected by the texture recognition sensor. The surface smoothness of the skin can intuitively reflect the health condition of the skin, so that the skin detection device can independently perform the health detection of the skin to be detected.

Optionally, the texture recognition sensor 02 can be a capacitive, optical or radio-frequency texture recognition sensor or a texture recognition sensor of other mode. The skin to be detected can be the facial skin or neck skin of the human body. The processor can be a general purpose processor (e.g., a central processing unit (CPU)) or a special purpose processor (a programmable logic circuit). No limitation will be given here in the embodiments of the present disclosure.

Figure 2:
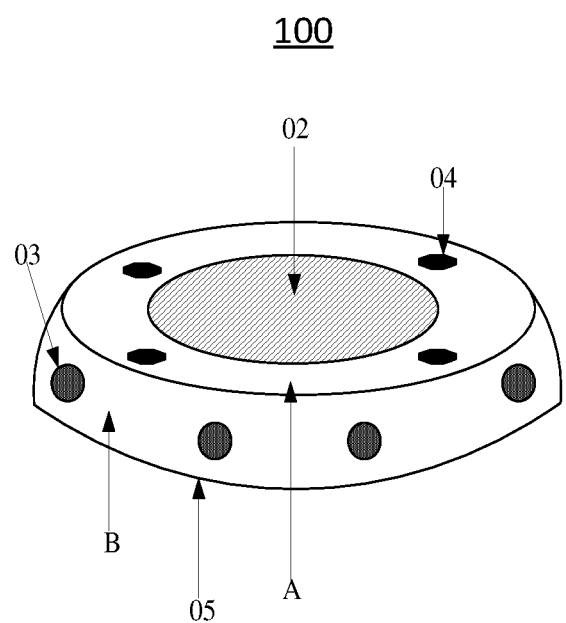
FIG. 2 is a schematic structural view of another skin detection device provided by the embodiments of the present disclosure.

FIG. 2 is a schematic structural view of another skin detection device provided by the embodiments of the present disclosure. As illustrated in FIG. 2, on the basis of the skin detection device as illustrated in FIG. 1, the skin detection device 100 further includes a first pressure sensor 03. The first pressure sensor 03, for example, can be a resistive or capacitive pressure sensor.

The first pressure sensor 03 can be configured to acquire the pressure applied to the first pressure sensor by the skin to be detected when the skin detection device slides on the skin to be detected. For example, in the case that the skin detection device slides on the skin to be detected so that there are wrinkles on the surface of the skin to be tested, the wrinkles will hinder the sliding of the skin detection device, and therefore the first pressure sensor 03 can be configured to acquire the pressure applied by the wrinkles in this case.

The processor (not illustrated in FIG. 2) can further be configured to determine the value of elasticity according to the pressure acquired by the first pressure sensor 03. Moreover, because the wrinkles of the skin caused by an external force are small in the case that the value of elasticity of the skin is high, the pressure detected by the first pressure sensor 03 is small in this case. Because the wrinkles of the skin caused by the external force are large in the case that the value of elasticity of the skin is low, the pressure detected by the first pressure sensor 03 is large in this case. Therefore, the processor can determine the value of elasticity of the skin to be detected according to the pressure detected by the first pressure sensor 03.

Optionally, the skin detection device 100 can further include: a detection electrode 04. The detection electrode 04 can be configured to acquire the conductivity of the skin to be detected by contacting the skin to be detected. Illustratively, the detection electrode 04 can be a metal pattern electrode. The conductivity of the skin is high in the case that the moisture content of the skin is large and the oil content of the skin is small, and the conductivity of the skin is low in the case that the moisture content of the skin is small and the oil content of the skin is low. Therefore, the processor can further be configured to determine the moisture content and the oil content of the skin to be detected according to the conductivity of the skin to be detected, and the conductivity of the skin to be detected is detected by the detection electrode.

Optionally, the skin detection device 100 can further include a base 05. The base 05 includes a contact surface A and a side surface B, and the contact surface A and the side surface B are connected. The contact surface A can be configured to contact the skin to be detected. Both the texture recognition sensor 02 and the detection electrode 04 can be disposed on the contact surface A, and the first pressure sensor 03 is disposed on the side surface B.

The texture recognition sensor 02 can be disposed in a central area of the contact surface A, and the detection electrode 04 can be disposed in a periphery area of the contact surface A. The material of the base 05 can be flexible material. In the case that the skin detection device contacts the skin to be detected, because the hardness of the base is low, scratching of the skin by the skin detection device can be effectively prevented, and the skin to be detected can have better touch. Moreover, in the case that the contact surface A contacts the skin to be detected, the side surface B is curved towards a side away from the skin to be detected, namely the side surface B is a curved surface. Therefore, in the case that the contact surface A on the base 05 contacts the skin to be detected, a connected part of the contact surface A and the side surface B is not angular, so the touch of the skin to be detected can be further improved.

Optionally, the skin detection device 100 can further include an image acquisitor (not illustrated in FIG. 2) such as a camera. The image acquisitor can be configured to acquire an image of the skin to be detected. The processor can further be configured to determine the colored patch distribution condition of the skin to be detected according to the image of the skin to be detected.

Figures 3, 4:
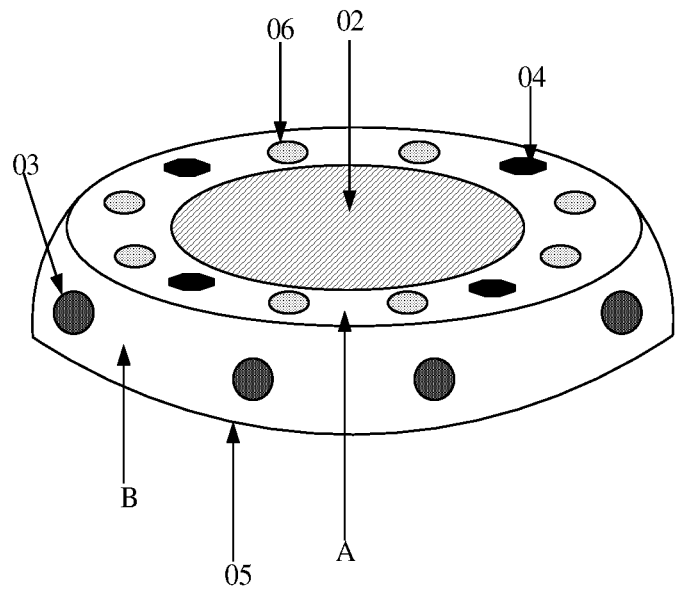
FIG. 3 is a schematic structural view of still another skin detection device provided by the embodiments of the present disclosure.
FIG. 4 is a flow chart of a product information determination method provided by the embodiments of the present disclosure.

Optionally, FIG. 3 is a schematic structural view of still another skin detection device provided by the embodiments of the present disclosure. As illustrated in FIG. 3, on the basis of the skin detection device as illustrated in FIG. 2, the skin detection device 100 can further include a second pressure sensor 06. The second pressure sensor 06 can be disposed on the contact surface A. Optionally, the number of the second pressure sensors 06 is the same with the number of the first pressure sensors 03, and the second pressure sensors 06 are in one-to-one correspondence with the first pressure sensors 03. In the case that the contact surface A of the skin detection device is circular, the center of the orthographic projection of one of the first pressure sensors 03, the center of the orthographic projection of a corresponding second pressure sensor 06, and the center of the contact surface A are located in the same straight line. Illustratively, eight first pressure sensors 03 and eight second pressure sensors 06 can be arranged in the skin detection device 100. The second pressure sensor 06 can be configured to detect the pressure applied to the second pressure sensor 06 by a portion of the skin to be detected in contact with the contact surface A.

The processor can further be configured to determine a target detection value according to the pressure detected by the first pressure sensor 03 and the pressure detected by the second pressure sensor 06, and determine the value of elasticity of the skin to be detected according to the target detection value. For example, in the case that the target detection value is greater than a preset threshold, the processor can determine that the value of elasticity of the skin to be detected is lower than a preset elasticity threshold, and in this case, the value of elasticity of the skin to be detected indicates a level of elasticity. Or the processor can directly determine the value of elasticity according to the target detection value, and in this case, the value of elasticity of the skin to be detected is a specific value.

Optionally, when determining of the target detection value, the processor can determine first pressure according to the pressure detected by the first pressure sensor 03, determine second pressure according to the pressure detected by the second pressure sensor 06, and determine the ratio of the first pressure to the second pressure as the target detection value. In specific implementations, the processor also can be configured to determine the difference between the first pressure and the second pressure as the target detection value. No limitation will be give here in the embodiments of the present disclosure. It should be noted that the processor can determine the first pressure and the second pressure by adoption of various implementations, and three implementations are described as follows.

In the first implementation, the first pressure is the sum of the pressure detected by all the first pressure sensors, and the second pressure is the sum of the pressure detected by all the second pressure sensors.

In the second implementation, the first pressure is the maximum pressure among the pressure detected by all the first pressure sensors, and the second pressure is the maximum pressure among the pressure detected by all the second pressure sensors.

In the third implementation, the first pressure is the pressure detected by a target first pressure sensor; the pressure detected by the target first pressure sensor is the maximum pressure among the pressure detected by all the first pressure sensors; and the second pressure is the pressure detected by the second pressure sensor corresponding to the target first pressure sensor.

The skin detection device 100 provided by the embodiments of the present disclosure can independently perform the detection of the skin to be detected, so as to determine the following information of the skin to be detected: the surface smoothness, the value of elasticity, the moisture content, the oil content and the colored patch distribution condition.

The skin detection device provided by the embodiments of the present disclosure includes the processor and the texture recognition sensor; the processor can determine the surface smoothness of the skin to be detected according to the surface texture of the skin to be detected, and the surface texture of the skin to be detected is detected by the texture recognition sensor; and the surface smoothness of the skin can intuitively reflect the health condition of the skin. Therefore, the skin detection device can independently perform the health detection of the skin to be detected.

FIG. 4 is a flow chart of a product information determination method provided by the embodiments of the present disclosure. As illustrated in FIG. 4, the product information determination method can include the following steps.

S401: acquiring collected data, in this step the collected data include data relevant to the skin to be detected and acquired by a skin detection device.

Optionally, the skin detection device can be the skin detection device as illustrated in FIG. 1, FIG. 2 or FIG. 3.

S402: determining product information, corresponding to at least one of the data in the collected data, according to preset corresponding relationships between the data and the product information.

In summary, in the product information determination method provided by the embodiments of the present disclosure, the collected data acquired includes the data relevant to the skin to be detected and acquired by the skin detection device; and the method determines the product information corresponding to the at least one of the data in the collected data according to the collected data and the preset corresponding relationships between the data and the product information, and then provides corresponding product information for the skin to be detected.

Figure 5:
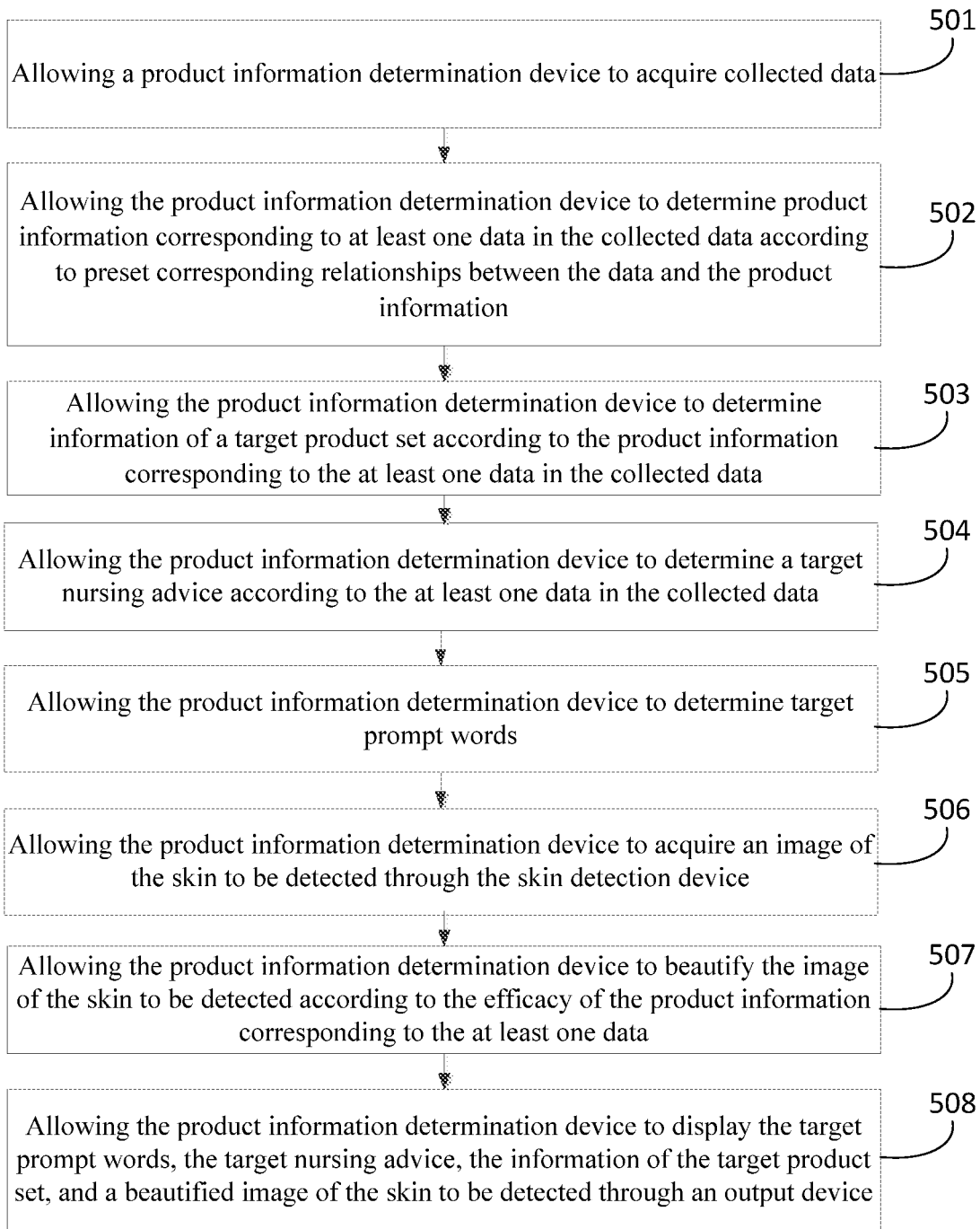
FIG. 5 is a flow chart of another product information determination method provided by the embodiments of the present disclosure.

FIG. 5 is a flow chart of another product information determination method provided by the embodiments of the present disclosure. As illustrated in FIG. 5, the product information determination method can include the following steps.

S501: acquiring collected data by a product information determination device.

Optionally, the product information determination device can be a computer or a cloud server. The collected data acquired by the product information determination device can include data relevant to the skin to be detected and acquired by a skin detection device. Optionally, the skin detection device can be the skin detection device as illustrated in FIG. 1, FIG. 2 or FIG. 3. The skin to be detected can be the skin of a target user. The collected data can further include attribute data of the target user. The attribute data can include attribute data such as name, age, gender, preference and purchasing power. The attribute data of the target user can be acquired by the product information determination device through an input device. Illustratively, the input device can include a keyboard, a mouse and a scanner.

Before executing the step S501, the product information determination device can further acquire verification information of the target user through a verification information acquisition device. Illustratively, the verification information of the target user can be: the cell-phone number of the target user, the fingerprint information of the target user, or the password set by the target user. Optionally, in the case that the verification information of the target user is the fingerprint information of the target user, the verification information acquisition device can be a fingerprint identification device.

In the process of executing the step S501, the product information determination device can determine whether or not a plurality of preset historical verification information includes the verification information of the target user. In the case that the plurality of preset historical verification information includes the verification information of the target user, the product information determination device can acquire historical data corresponding to the verification information of the target user according to preset corresponding relationships between the historical verification information and the historical data. In this case, the collected data acquired in the step S501 can further include: the historical data corresponding to the verification information of the target user.

Illustratively, an initial signal can carry the data relevant to the skin to be detected and acquired by the skin detection device, and after the skin detection device acquires the data relevant to the skin to be detected, the skin detection device can send the initial signal carrying the data relevant to the skin to be detected to a signal amplifying device. The signal amplifying device can obtain a target signal by amplifying the initial signal, and send the target signal to the product information determination device, so that the product information determination device can extract the data relevant to the skin to be detected in the collected data from the target signal.

S502: determining product information corresponding to at least one of the data in the collected data according to preset corresponding relationships between the data and the product information by the product information determination device.

After acquiring the collected data, the product information determination device can determine the product information corresponding to the at least one of the data in the collected data according to the preset corresponding relationships between the data and the product information. Illustratively, the product information determination device can determine the product information corresponding to each data in the collected data according to the preset corresponding relationships between the data and the product information. No limitation will be given here in the embodiments of the present disclosure.

For example, the data in the preset corresponding relationships between the data and the product information can include: the smoothness X1 and the smoothness X2 and the smoothness X1 is greater than the smoothness X2; the smoothness X1 corresponds to product information of a product Y1 and the product Y1 can achieve a slight tightening effect on the skin and improve the smoothness; the smoothness X2 corresponds to product information of a product Y2 and the product Y2 can achieve a large tightening effect on the skin and improve the smoothness.

S503: determining information of a target product set according to the product information corresponding to the at least one of the data in the collected data by the product information determination device.

Illustratively, in the process of determining the information of the target product set, on one hand, the product information determination device can obtain the information of the target product set from information of at least one preset product set, and the information of the target product set can include the product information corresponding to the at least one of the data, mentioned in the step S502. For example, the information of the target product set includes: information of a product Z1, information of a product Z2, and information of a product Z3. The product information corresponding to the at least one of the data belongs to: a collection of the information of the product Z1, the information of the product Z2, and the information of the product Z3.

On the other hand, the product information determination device can further obtain the information of the target product set by the redundancy elimination of the product information corresponding to the at least one of the data. For example, the product information corresponding to the at least one of the data can be: the information of the product Z1, the information of the product Z1, the information of the product Z2, and the information of the product Z3, and in this case, after the information of the product Z1 is deleted by redundancy elimination through the product information determination device, the obtained information of the target product set is: the information of the product Z1, the information of the product Z2, and the information of the product Z3.

S504: determining a target nursing advice according to the at least one of the data in the collected data by the product information determination device.

The product information determination device can also determine nursing advices corresponding to the at least one of the data mentioned in the step S502 according to preset corresponding relationships between the data and the nursing advices, and combine one or more of nursing advices corresponding to the at least one of the data into the target nursing advice. For example, if the nursing advices corresponding to the at least one of the data are respectively: a nursing advice 1 (drinking more water), a nursing advice 2 (washing your face frequently), a nursing advice 3 (eating more vegetables) and a nursing advice 4 (exercising more), the target nursing advice can be: drinking more water, washing your face frequently, eating more vegetables, and exercising more.

S505: determining target prompt words by the product information determination device.

Illustratively, the product information determination device can acquire a face image of the target user through a camera. Subsequently, the product information determination device can determine the emotional level of the target user (namely determining whether the current emotion of the target user is good or not good) by analyzing the face image of the target user. The product information determination device can also determine the age bracket of the target user according to the attribute data of the target user, and then determine the target prompt words corresponding to the age bracket and the emotional level of the target user according to preset corresponding relationships between the prompt words and the age bracket, and between the prompt words and emotional level.

The product information determination device can determine the prompt words that the target user currently prefers according to the bracket and the emotion, so as to improve the reading experience of the target user while seeing the prompt words.

S506: acquiring an image of the skin to be detected through the skin detection device by the product information determination device.

Illustratively, the product information determination device can also acquire the image (the image can be an image of part of the skin to be detected) of the skin to be detected through the skin detection device.

S507: beautifying the image of the skin to be detected according to the efficacy of the product information corresponding to the at least one of the data by the product information determination device.

The product information can relate to a product, and each product has its own efficacy. After determining the product information corresponding to the at least one of the data, mentioned in the step S502, the product information determination device can also determine the efficacy of the product information corresponding to the at least one of the data, and then beautify the image of the skin to be detected (namely image beautifying) according to the efficacy of the product information corresponding to the at least one of the data.

For example, if the efficacy of the product information corresponding to the at least one of the data includes: anti-acne, the product information determination device can perform skin smoothing on the image of the skin to be detected to eliminate the acne in the image of the skin to be detected.

S508: displaying the target prompt words, the target nursing advice, the information of the target product set, and a beautified image of the skin to be detected through an output device and by the product information determination device.

After obtaining the target prompt words, the target nursing advice, the information of the target product set, and the beautified image of the skin to be detected, the product information determination device can display at least one of the target prompt words, the target nursing advice, the information of the target product set, or the beautified image of the skin to be detected through the output device. Illustratively, the output device can include: at least one of a display component, a print component or a voice playback component.

In summary, in the product information determination method provided by the embodiments of the present disclosure, the collected data acquired by the product information determination device includes: the data relevant to the skin to be detected and acquired by the skin detection device; and the method determines the product information corresponding to the at least one of the data in the collected data according to the collected data and the preset corresponding relationships between the data and the product information, and then provides corresponding product information for the skin to be detected.

Figure 6:
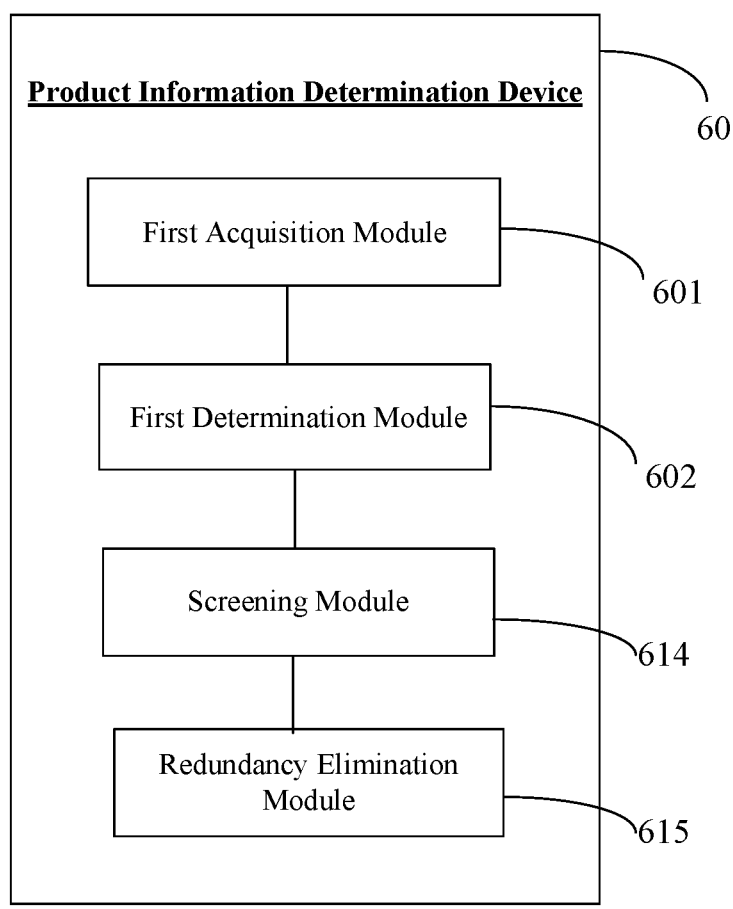
FIG. 6 is a schematic structural view of a product information determination device provided by the embodiments of the present disclosure.

FIG. 6 is a schematic structural view of a product information determination device provided by the embodiments of the present disclosure. As illustrated in FIG. 6, the product information determination device 60 can include: a first acquisition module 601 and a first determination module 602.

The first acquisition module 601 is configured to acquire collected data. The first acquisition module 601 can be a skin detection device including, for example, the texture recognition sensor, the pressure sensor or the detection electrode in the above-mentioned embodiments; the collected data include: data relevant to the skin to be detected and acquired by the skin detection device; the skin detection device is any one of the skin detection device provided by the embodiments of the present disclosure.

The first determination module 602 is configured to determine product information corresponding to at least one of the data in the collected data according to preset corresponding relationships between the data and the product information. The first determination module 602, for example, can be a processor in the above-mentioned embodiments, a software program, or a combination of hardware and software In summary, in the product information determination device provided by the embodiments of the present disclosure, the collected data acquired by the first acquisition module includes: the data relevant to the skin to be detected and acquired by the skin detection device; and the first determination module determines the product information corresponding to the at least one of the data in the collected data according to the collected data and the preset corresponding relationships between the data and the product information, and then provides corresponding product information for the skin to be detected.

Optionally, the product information determination device 60 as illustrated in FIG. 6 can further include: a screening module 614 configured to obtain information of a target product set in information from at least one preset product set. The information of the target product set includes the product information corresponding to the at least one of the data.

Optionally, the product information determination device 60 as illustrated in FIG. 6 can further include: a redundancy elimination module 615 configured to obtain the information of the target product set by the redundancy elimination of the product information corresponding to the at least one of the data.

Figure 7:
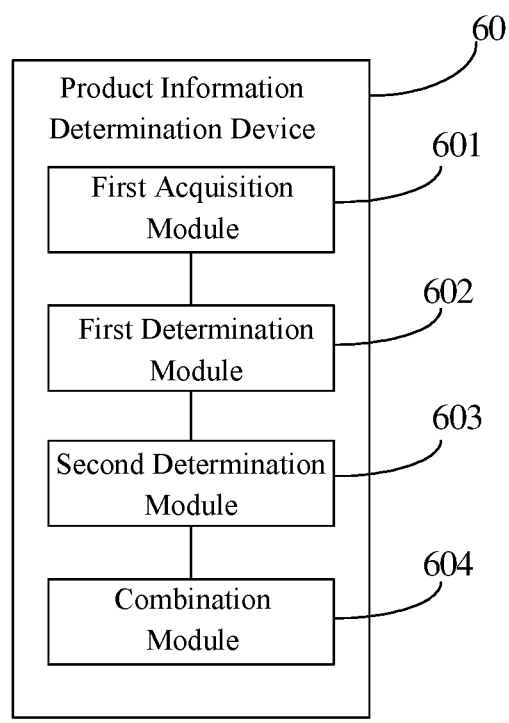
FIG. 7 is a schematic structural view of another product information determination device provided by the embodiments of the present disclosure.

Optionally, FIG. 7 is a schematic structural view of another product information determination device provided by the embodiments of the present disclosure. As illustrated in FIG. 7, on the basis of FIG. 6, the product information determination device 60 can further include a second determination module 603 and a combination module 604.

The second determination module 603 is configured to determine nursing advices corresponding to at least one of the data according to preset corresponding relationships between the data and the nursing advices. The second determination module 603, for example, can be a processor in the above-mentioned embodiments, a software program, or a combination of software and hardware, The combination module 604 is configured to combine the nursing advices corresponding to the at least one of the data into a target nursing advice.

Optionally, the skin to be detected is the skin of a target user; the collected data further include: attribute data of the target user; and the attribute data include: attribute data such as name, age, gender, preference and purchasing power.

Figure 8:
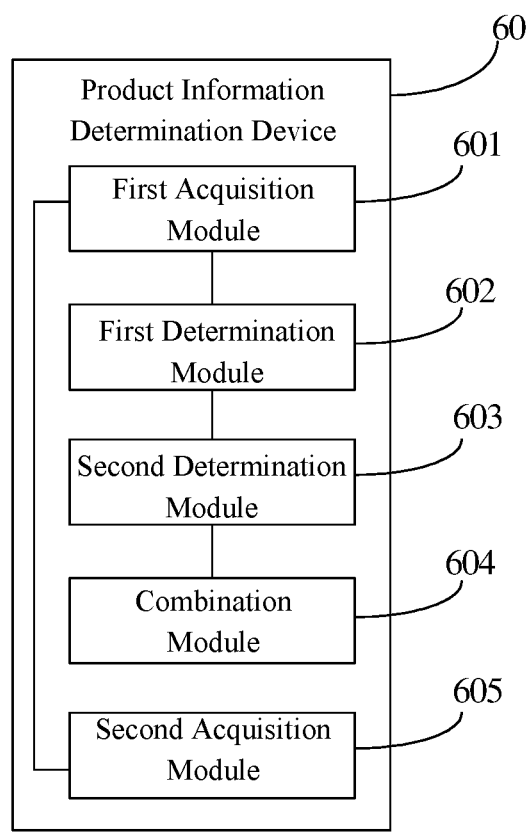
FIG. 8 is a schematic structural view of still another product information determination device provided by the embodiments of the present disclosure.

Optionally, FIG. 8 is a schematic structural view of still another product information determination device provided by the embodiments of the present disclosure. As illustrated in FIG. 8, on the basis of FIG. 7, the product information determination device 60 can further include: a second acquisition module 605 configured to acquire verification information of a target user through a verification information acquisition device. The second acquisition module 605, for example, can be an input keyboard, a texture recognition sensor, an iris recognition sensor, software (the software is implemented by a computer program for acquiring the verification information), or a combination of software and hardware.

The first acquisition module 601 can further be configured to: determine whether or not a plurality of preset historical verification information includes the verification information of the target user, and acquire historical data corresponding to the verification information of the target user according to preset corresponding relationships between the historical verification information and the historical data in the case that the plurality of historical verification information includes the verification information of the target user. The collected data further include: the historical data corresponding to the verification information of the target user.

Figure 9:
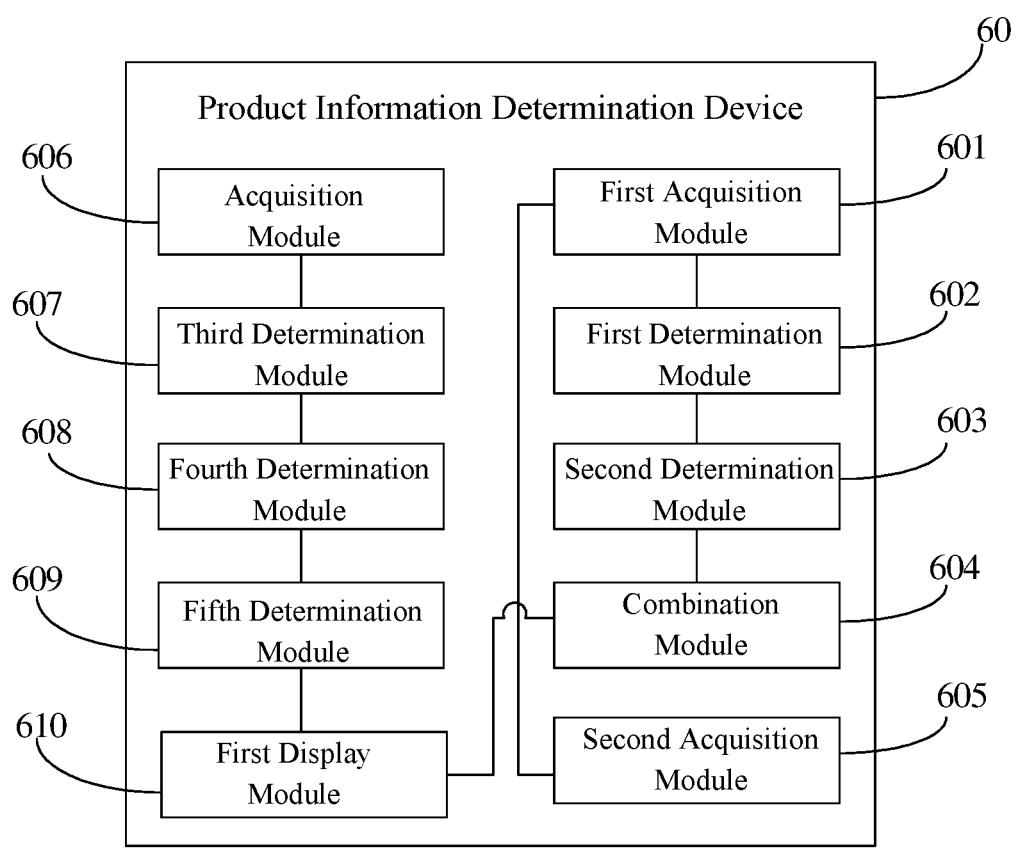
FIG. 9 is a schematic structural view of still another product information determination device provided by the embodiments of the present disclosure.

Optionally, FIG. 9 is a schematic structural view of still another product information determination device provided by the embodiments of the present disclosure. As illustrated in FIG. 9, on the basis of FIG. 8, the product information determination device 60 can further include: an acquisition module 606, a third determination module 607, a fourth determination module 608, a fifth determination module 609, and a first display module 610.

The acquisition module 606 (e.g., a camera) is configured to acquire a face image of a target user through a camera.

The third determination module 607 (e.g., a processor, a software program, or a combination of software and hardware) is configured to determine the emotional level of the target user according to the face image of the target user.

The fourth determination module 608 (e.g., a processor, a software program, or a combination of software and hardware) is configured to determine the age bracket of the target user.

The fifth determination module 609 (e.g., a processor, a software program, or a combination of software and hardware) is configured to determine target prompt words corresponding to the age bracket of the target user and the emotional level of the target user according to preset corresponding relationships between the prompt words and the age bracket, and between the prompt words and emotional level.

The first display module 610 (e.g., a display) is configured to display the target prompt words, a target nursing advice, and information of a target product set through an output device.

Figure 10:
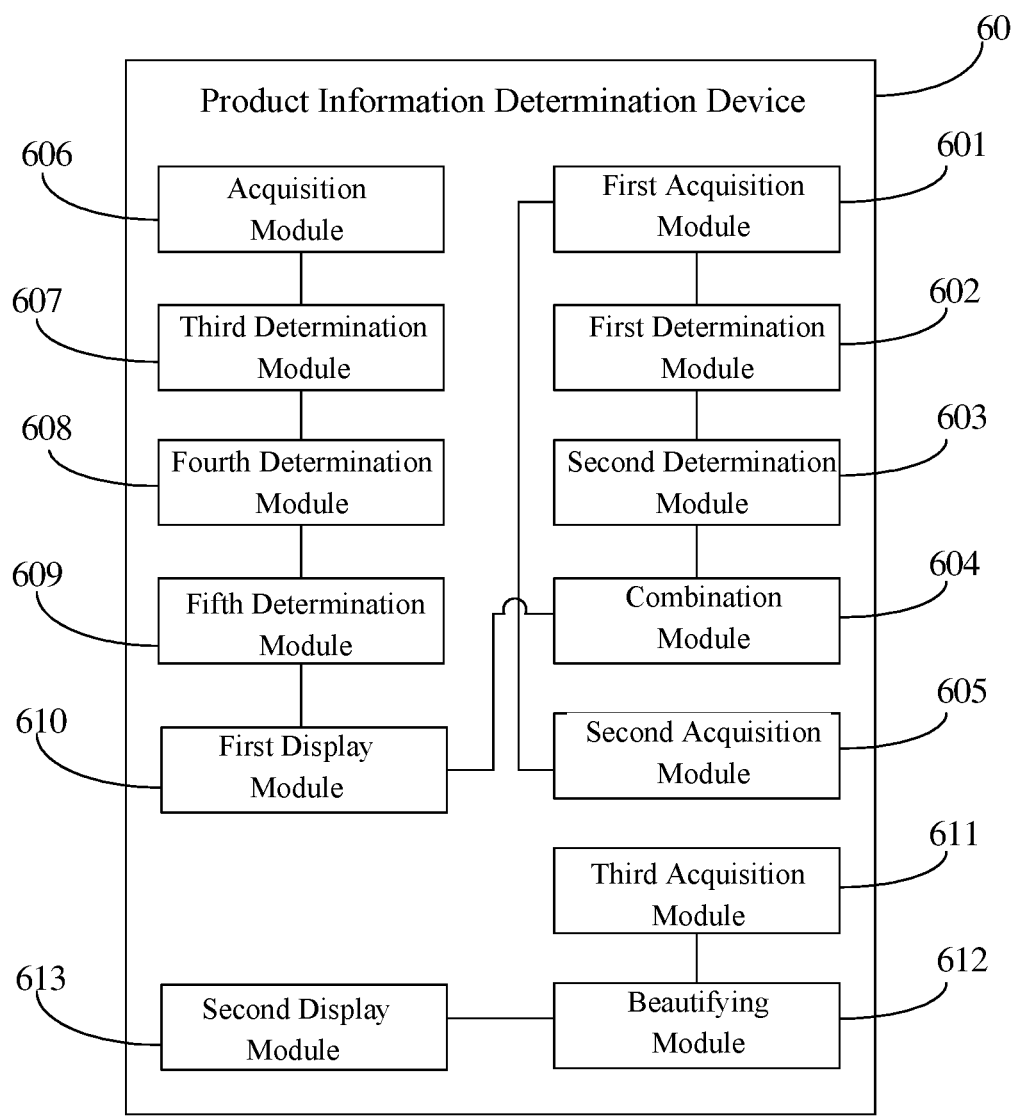
FIG. 10 is a schematic structural view of a product information determination device provided by another embodiment of the present disclosure.

Optionally, FIG. 10 is a schematic structural view of a product information determination device provided by another embodiment of the present disclosure. As illustrated in FIG. 10, on the basis of FIG. 9, the product information determination device 60 can further include: a third acquisition module 611, a beautifying module 612 and a second display module 613.

The third acquisition module 611 (e.g., the skin detection device provided by the above-mentioned embodiment) is configured to acquire an image of the skin to be detected through a skin detection device.

The beautifying module 612 (e.g., an image processor) configured to beautify the image of the skin to be detected according to the efficacy of product information corresponding to at least one of the data.

The second display module 613 (e.g., a display, a display program, or a combination of the display and the display program) is configured to display a beautified image of the skin to be detected through an output device.

Optionally, the first acquisition module 601 can further be configured to: acquire a target signal obtained by amplifying an initial signal through a signal amplifying device, and the initial signal includes data relevant to the skin to be detected and acquired by the skin detection device; and extract the data relevant to the skin to be detected from the target signal.

In summary, in the product information determination device provided by the embodiments of the present disclosure, the collected data acquired by the first acquisition module includes: the data relevant to the skin to be detected and acquired by the skin detection device; and the first determination module determines the product information corresponding to the at least one of the data in the collected data according to the collected data and preset corresponding relationships between the data and the product information, and then provides corresponding product information for the skin to be detected.

Figure 11:
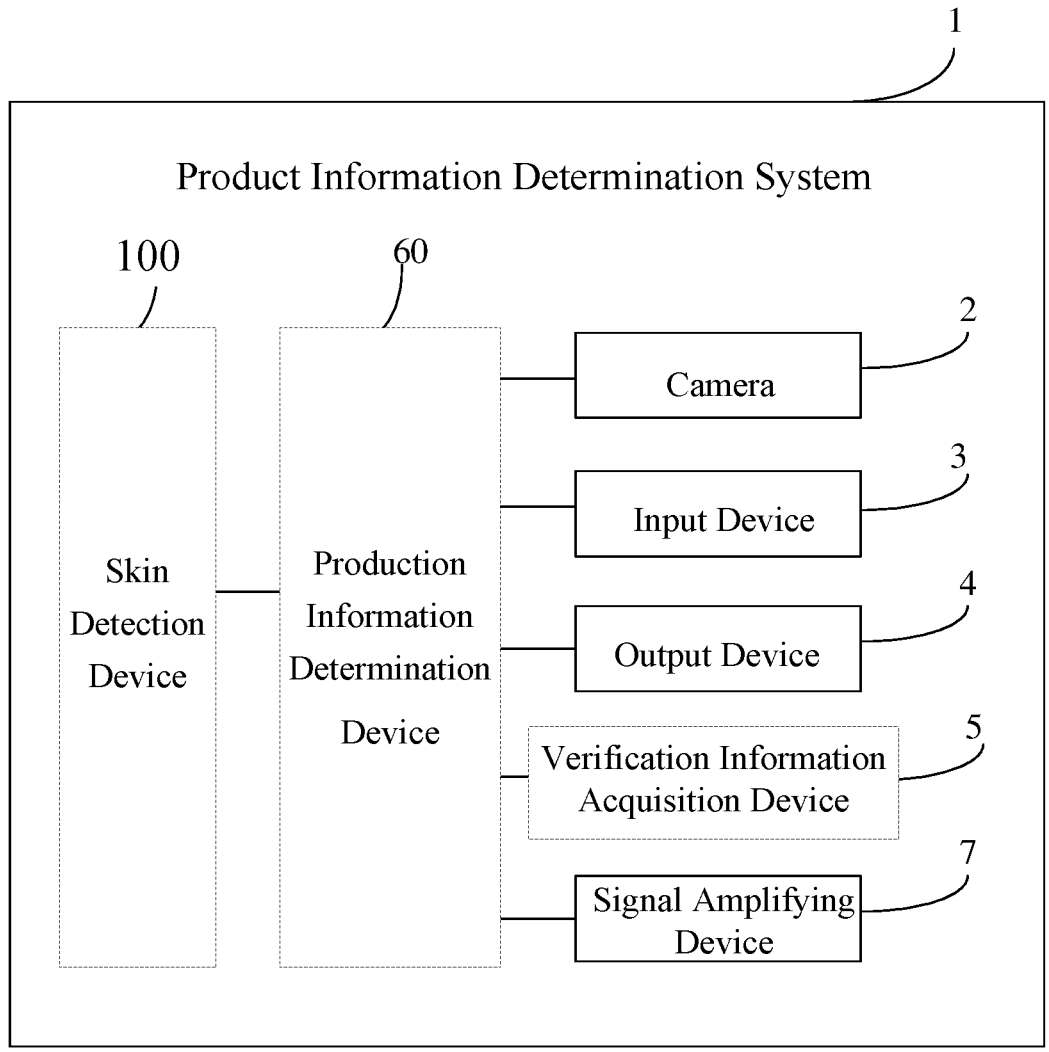
FIG. 11 is a schematic structural view of a product information determination system provided by the embodiments of the present disclosure.

FIG. 11 is a schematic structural view of a product information determination system provided by the embodiments of the present disclosure. As illustrated in FIG. 11, the product information determination system 1 can include: a skin detection device 100 and a product information determination device 60. The skin detection device 100 can be the skin detection device as illustrated in FIG. 1, FIG. 2 or FIG. 3. The product information determination device 60 can be any product information determination device as illustrated in FIGS. 6 to 10.

Optionally, the product information determination system 1 can further include: a camera 2, an input device 3 (e.g., a keyboard or a mouse), an output device 4 (e.g., a display), a verification information acquisition device 5 (e.g., a fingerprint reader, a keyboard or an iris recognizer) and a signal amplifying device 7.

The camera 2 is configured to acquire a face image of a target user. The skin of the target user is the skin to be detected. The input device 3 is configured to input the following information into the product information determination device 60: preset corresponding relationships between data and product information, preset corresponding relationships between the data and nursing advices, preset corresponding relationships between the prompt words and the age bracket, and between the prompt words and emotional level, information of at least one preset product set, and attribute data of the target user. The verification information acquisition device 5 can be configured to acquire verification information of the target user. The signal amplifying device 7 can be configured to amplify the initial signal and obtain a target signal, and the initial signal carries data relevant to the skin to be detected and acquired by the skin detection device. The output device 4 can be configured to display one or more of the following information obtained by the product information determination device: target prompt words, a target nursing advice, information of a target product set, and a beautified image of the skin to be detected.

Figure 12:
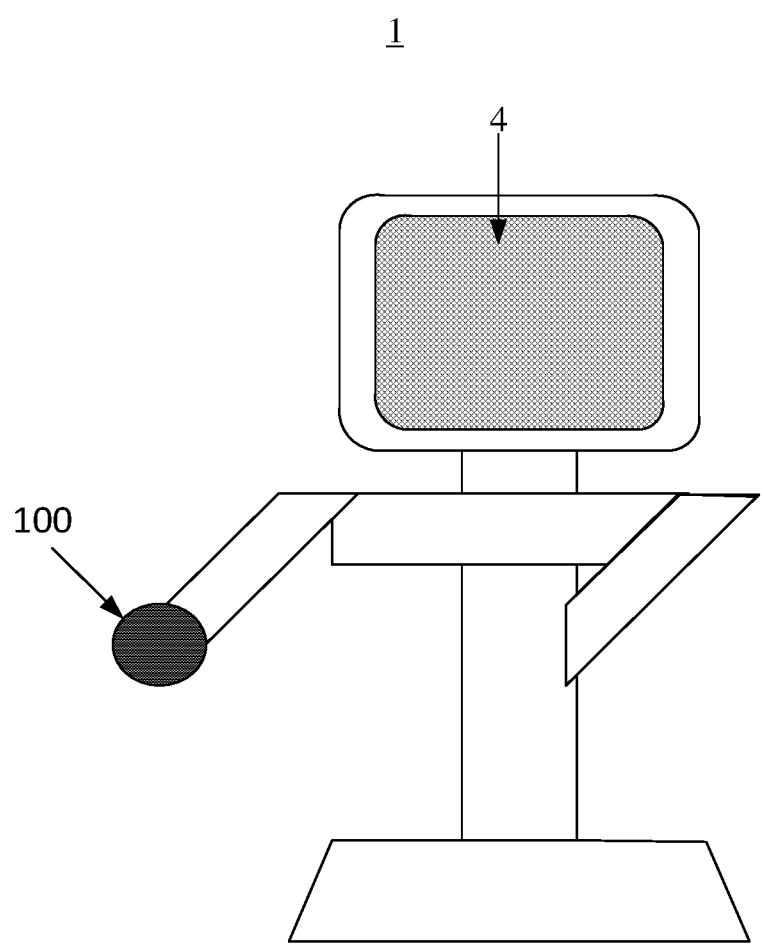
FIG. 12 is a schematic structural view illustrating part of a product information determination system provided by the embodiments of the present disclosure.

Illustratively, FIG. 12 is a schematic structural view of part of a product information determination system 1 provided by the embodiments of the present disclosure. As illustrated in FIG. 12, the output device 4 can be a display component. The skin detection device can be electrically connected with the output device 4.

In summary, in the product information determination system provided by the embodiments of the present disclosure, the collected data acquired by the product information determination device includes: the data relevant to the skin to be detected and acquired by the skin detection device; and the system determines the product information corresponding to the at least one of the data in the collected data according to the collected data and the preset corresponding relationships between the data and the product information, and then provides corresponding product information for the skin to be detected.

The above-mentioned embodiment can be entirely or partially implemented by software, hardware, firmware or any combination thereof. When implemented by software, the embodiment can be entirely or partially implemented by a computer program product, and the computer program product includes one or more computer instruction. When the computer program instruction is loaded and executed on a computer, the flowcharts or the functions in the embodiments of the present disclosure are entirely or partially performed. The computer can be a general purpose computer, a computer network, or other programmable device. The computer instruction can be stored in a readable storage medium of a computer or transmitted from one computer readable storage medium to another computer readable storage medium. For example, the computer instruction can be transmitted from a website site, a computer, a server or a data center to another website site, computer, server, or data center by wired (e.g., a coaxial cable, an optical fiber or a digital subscriber line) or wireless (e.g., infrared, wireless or microwave) means. The computer readable storage medium can be any available medium that can be accessed by a computer or a data storage device such as a server, a data center, or the like that is formed by one or more available media. The available medium can be a magnetic medium (for example, a floppy disk, a hard disk or a magnetic tape), an optical medium, or a semiconductor medium (e.g., a solid-state drive).

The numerals of the embodiments of the present disclosure are only used for description and do not represent qualities of the embodiments.

It should be noted that the embodiments of the skin detection device, the embodiments of the product information determination method, the embodiments of the product information determination device, and the embodiments of the product information determination system provided by the embodiments of the present disclosure can refer to each other. No limitation will be given here in the embodiments of the present disclosure.

It should be understood by those skilled in the art that all or part of the steps for implementing the above-mentioned embodiments can be independently performed by hardware and can also be independently perform by adoption of a program to instruct related hardware. The program can be stored in a computer readable storage medium. The storage medium mentioned above can be a read only memory (ROM), a magnetic disk, an optical disk, etc.

The foregoing is only the preferred embodiments of the present disclosure and not intended to limit the present disclosure. Any change, equivalent replacement, improvement or the like made within the spirit and the principle of the present disclosure shall fall within the scope of protection of the present disclosure.

The application claims priority to Chinese patent application No. 201710517873.3, filed on Jun. 29, 2017, the entire disclosure of which is incorporated herein by reference as part of the present application.

What is claimed is:

1. A skin detection device, comprising: a processor and a texture recognition sensor, wherein
the processor is electrically connected with the texture recognition sensor;
the texture recognition sensor is configured to detect surface texture of skin to be detected; and
the processor is configured to determine surface smoothness of the skin to be detected according to the surface texture of the skin to be detected,
the skin detection device further comprises a first pressure sensor, wherein
the first pressure sensor is electrically connected with the processor and is configured to acquire pressure applied by the skin to be detected to the first pressure sensor when the skin detection device slides on the skin to be detected; and
the processor is further configured to determine a value of elasticity of the skin to be detected according to the pressure acquired by the first pressure sensor,
the skin detection device further comprises: a detection electrode electrically connected with the processor, wherein
the detection electrode is configured to acquire conductivity of the skin to be detected by contacting the skin to be detected; and
the processor is further configured to determine moisture content and oil content of the skin to be detected according to the conductivity, the skin detection device further comprises: a base, wherein
the base comprises a contact surface and a side surface, and the contact surface and the side surface are connected;
the contact surface is configured to contact the skin to be detected;
the texture recognition sensor and the detection electrode are disposed on the contact surface; and
the first pressure sensor is disposed on the side surface,
the skin detection device further comprises: a second pressure sensor, wherein
the second pressure sensor is disposed on the contact surface and configured to detect pressure applied to the second pressure sensor by a portion of the skin to be detected in contact with the contact surface;
the processor is further configured to determine a target detection value according to the pressure detected by the first pressure sensor and the pressure detected by the second pressure sensor; and
the processor is further configured to determine the value of elasticity of the skin to be detected according to the target detection value.

2. The skin detection device according to claim 1, wherein the second pressure sensors are in one-to-one correspondence with the first pressure sensors.

3. The skin detection device according to claim 1, wherein the texture recognition sensor is disposed in a central area of the contact surface; and the detection electrode is disposed in a periphery area of the contact surface;
a material of the base is a flexible material; and
the side surface is curved towards a side away from the skin to be detected, when the contact surface contacts the skin to be detected.

4. The skin detection device according to claim 1, further comprising: an image acquisitor electrically connected with the processor,
wherein the image acquisitor is configured to acquire an image of the skin to be detected; and
the processor is further configured to determine colored patch distribution condition of the skin to be detected according to the image of the skin to be detected.

5. A product information determination method, comprising:
acquiring collected data, wherein the collected data comprise data relevant to the skin to be detected and acquired by the skin detection device according to claim 1; and
determining product information, corresponding to at least one of the data in the collected data, according to preset corresponding relationships between the data and the product information.

6. The method according to claim 5, further comprising: obtaining information of a target product set from information of at least one preset product set, after determining of the product information corresponding to the at least one of the data in the collected data,
wherein the information of the target product set comprises the product information corresponding to the at least one of the data.

7. The method according to claim 5, further comprising: obtaining information of a target product set by redundancy elimination of the product information corresponding to the at least one of the data, after determining of the product information corresponding to the at least one of the data in the collected data.

8. The method according to claim 6, wherein after acquiring of the collected data, the method further comprises:
determining nursing advices corresponding to the at least one of the data according to preset corresponding relationships between the data and the nursing advices; and
obtaining a target nursing advice through combining one or more of the nursing advices corresponding to the at least one of the data.

9. The method according to claim 8, wherein the skin to be detected is skin of a target user;
the collected data further comprise attribute data of the target user; and
the attribute data comprise at least one of name, age, gender, preference and purchasing power.

10. The method according to claim 9, further comprising: acquiring verification information of the target user through a verification information acquisition device before acquiring of the collected data,
wherein acquiring of the collected data comprises:
determining whether or not a plurality of preset historical verification information comprises the verification information of the target user; and
acquiring historical data corresponding to the verification information of the target user according to preset corresponding relationships between the historical verification information and the historical data in a case that the plurality of historical verification information comprises the verification information of the target user, wherein the collected data further comprise the historical data corresponding to the verification information of the target user.

11. The method according to claim 10, further comprising:
acquiring a face image of the target user through a camera;
determining emotional level of the target user according to the face image of the target user;
determining age bracket of the target user;
determining target prompt words corresponding to the age bracket and the emotional level of the target user according to preset corresponding relationships between the prompt words and the age bracket, and between the prompt words and emotional level; and
displaying at least one of the target prompt words, the target nursing advice, and the information of the target product set through an output device;
acquiring an image of the skin to be detected through the skin detection device; and
beautifying the image of the skin to be detected according to efficacy of the product information corresponding to the at least one of the data after determining of the product information corresponding to the at least one of the data in the collected data, and displaying a beautified image of the skin to be detected through the output device.

12. The method according to claim 5, wherein acquiring of the collected data comprises:
acquiring a target signal obtained by amplifying an initial signal through a signal amplifying device, wherein the initial signal comprise the data relevant to the skin to be detected and acquired by the skin detection device; and
extracting the data relevant to the skin to be detected from the target signal.

13. A product information determination device, comprising:
- a first acquisition module configured to acquire collected data, wherein the collected data comprise: data relevant to skin to be detected and acquired by the skin detection device according to claim 1; and
- a first determination module configured to determine product information corresponding to at least one of the data in the collected data according to preset corresponding relationships between the data and the product information.

14. The product information determination device according to claim 13, further comprising:
- a screening module configured to obtain information of a target product set from information of at least one preset product set, wherein the information of the target product set comprises the product information corresponding to the at least one of the data;
- a redundancy elimination module configured to obtain information of a target product set by redundancy elimination of the product information corresponding to the at least one of the data;
- a second determination module configured to determine nursing advices corresponding to the at least one of the data according to preset corresponding relationships between the data and the nursing advices;
- a combination module configured to obtain a target nursing advice through combining one or more of the nursing advices corresponding to the at least one of the data;
- the skin to be detected is skin of a target user;
- the collected data further comprise attribute data of the target user;
- the attribute data comprise: name, age, gender, preference and purchasing power;
- a second acquisition module configured to acquire verification information of the target user through a verification information acquisition device;
- an acquisition module configured to acquire a face image of the target user through a camera;
- a third determination module configured to determine emotional level of the target user according to the face image of the target user;
- a fourth determination module configured to determine age bracket of the target user;
- a fifth determination module configured to determine target prompt words corresponding to the age bracket and the emotional level of the target user according to preset corresponding relationships between the prompt words and the age bracket and emotional level;
- a first display module configured to display at least one of the target prompt words, the target nursing advice, and the information of the target product set through an output device;
- a third acquisition module configured to acquire an image of the skin to be detected through the skin detection device;
- a beautifying module configured to beautify the image of the skin to be detected according to efficacy of the product information corresponding to the at least one of the data; and
- a second display module configured to display a beautified image of the skin to be detected through the output device, wherein the first acquisition module is further configured to:
- determine whether or not a plurality of preset historical verification information comprises the verification information of the target user, and acquire historical data corresponding to the verification information of the target user according to preset corresponding relationships between the historical verification information and the historical data in a case that the plurality of historical verification information comprises the verification information of the target user, wherein the collected data further comprise the historical data corresponding to the verification information of the target user;

the first acquisition module is further configured to:
- acquire a target signal obtained by amplifying an initial signal through a signal amplifying device, and extracting the data relevant to the skin to be detected from the target signal; and
- the initial signal carries the data relevant to the skin to be detected and acquired by the skin detection device.

15. A product information determination system, comprising: a skin detection device, and a product information determination device according to claim 13, wherein
- the skin detection device comprises a processor and a texture recognition sensor;
- the texture recognition sensor is electrically connected with the processor and configured to detect surface texture of skin to be detected; and
- the processor is configured to determine surface smoothness of the skin to be detected according to the surface texture of the skin to be detected.

16. The product information determination system according to claim 15, further comprising: a camera, an input device, an output device, a verification information acquisition device and a signal amplifying device, wherein
- the camera is configured to acquire a face image of a target user, and the skin to be detected is skin of the target user;
- the input device is configured to input at least one of following information into the product information determination device: preset corresponding relationships between data and product information, preset corresponding relationships between the data and nursing advices, preset corresponding relationships between prompt words and age bracket, and between prompt words and emotional level, information of at least one preset product set, and attribute data of the target user;
- the verification information acquisition device is configured to acquire verification information of the target user;
- the signal amplifying device is configured to amplify an initial signal and obtain a target signal, wherein the initial signal carries data relevant to the skin to be detected and acquired by the skin detection device; and
- the output device is configured to display at least one of following information obtained by the product information determination device: target prompt words, a target nursing advice, information of a target product set, or a beautified image of the skin to be detected.

* * * * *